United States Patent [19]

Michaels

[11] 4,237,893

[45] Dec. 9, 1980

[54] CERVICAL DILATOR

[75] Inventor: Alan S. Michaels, San Francisco, Calif.

[73] Assignee: Alza Corporation, Palo Alto, Calif.

[21] Appl. No.: 97,928

[22] Filed: Nov. 28, 1979

Related U.S. Application Data

[63] Continuation of Ser. No. 844,967, Oct. 25, 1977, abandoned.

[51] Int. Cl.³ ............................................. A61M 29/00
[52] U.S. Cl. ...................................... 128/341; 128/130
[58] Field of Search .............................. 128/127–130, 128/270, 285, 303, 341, 344

[56] References Cited

U.S. PATENT DOCUMENTS

| 1,887,526 | 11/1932 | Spielberg | 128/285 |
|---|---|---|---|
| 3,722,500 | 3/1973 | Wichterle | 128/260 |
| 3,760,984 | 9/1973 | Theeuwes | 222/95 |
| 3,865,108 | 2/1975 | Hartop | 128/270 |
| 3,971,376 | 7/1976 | Wichterle | 128/260 |
| 3,971,379 | 7/1976 | Chatterjee | 128/285 |
| 3,987,790 | 10/1976 | Eckenhoff | 128/260 |
| 3,991,760 | 11/1976 | Drobish et al. | 128/129 |
| 3,993,551 | 11/1976 | Assarsson et al. | 128/285 |
| 3,995,631 | 12/1976 | Higuchi et al. | 128/260 |
| 4,017,653 | 4/1977 | Gross | 128/285 |
| 4,041,948 | 8/1977 | Flam et al. | 128/270 |
| 4,061,846 | 12/1977 | Gross et al. | 128/270 |
| 4,137,922 | 2/1979 | Leininger et al. | 128/344 |

FOREIGN PATENT DOCUMENTS 773276  1/1972  Belgium ................................ 128/285

*Primary Examiner*—C. Fred Rosenbaum
*Attorney, Agent, or Firm*—Paul L. Sabatine; Edward L. Mandell; Thomas E. Ciotti

[57] ABSTRACT

A self-powered cervical dilator is disclosed. The dilator comprises (1) an expandable housing positioned around (2) a swellable laminate, which laminate surrounds (3) a support member. The laminate comprises (a) a lamina formed of an absorbent material laminated to (b) a lamina formed of a swellable polymer facing the housing. In operation, when the dilator is in the cervical canal, fluid therefrom is imbibed by the laminate into the dilator causing the laminate to swell and apply pressure against and expand the housing, which housing correspondingly exerts force against the walls of the cervical canal thereby dilating the canal.

7 Claims, 5 Drawing Figures

CERVICAL DILATOR

CROSS REFERENCE TO RELATED APPLICATION

This application is a continuation of U.S. application Ser. No. 844,967 filed on Oct. 25, 1977, now abandoned, which application is incorporated herein by reference and benefit is claimed of its filing date. This application and Ser. No. 844,967 both are assigned to the ALZA Corporation of Palo Alto, Calif.

FIELD OF THE INVENTION

The present invention pertains to both a novel and useful dilator adapted for insertion into and for enlarging the cervical canal.

BACKGROUND OF THE INVENTION

In gynecological and obstetrical practice, it is frequently necessary to dilate the cervical canal for performing many medical and surgical procedures. The method presently used for dilating the canal consists of introducing a dilator into the canal that increases its dimensions and concomitantly enlarges the canal. A critical need exists for a cervical dilator that can be used with relative comfort and ease for effecting this purpose. The current dilators used for enlarging the cervical canal generally possess a number of shortcomings that tend to limit their acceptance. For example, the dilators described in *Stedman's Medical Dictionary*, 21st Edition, pages 448 to 449, 1966 include the Bossi dilator consisting of blunt-pointed metallic rods separated by a registering screw, and the Hegar dilator consisting of a series of rodlike instruments of increasing diameters, evident shortcomings as they are often used with a distressing amount of pain and trauma, and their use requires considerable skill to produce dilation without injuring the tissues of the reproductive system. In view of the above presentation, it will be appreciated by those versed in the art that a critical need exists for a dilator that is simple in construction, easy to manufacture, and can be easily used with a minimum of personal discomfort.

OBJECTS OF THE INVENTION

Accordingly, it is an immediate object of this invention to make available a new and useful cervical dilator that overcomes the shortcomings known to the prior art.

Another object of the invention is to provide a cervical dilator that is simple in construction, inexpensive to manufacture, produces practical benefits, and is disposable.

Yet another object of the invention is to provide a dilator that is efficient for cervical dilation, can be used with diminished discomfort and trauma, and easily removed from the environment of use.

Other objects, features and advantages of this invention will become more apparent from the following description when taken in conjunction with the accompanying specification, the drawings and the claims.

SUMMARY OF THE INVENTION

The invention concerns a dilator for enlarging the cervical canal. The dilator comprises a swellable laminate, optionally surrounding a support base, positioned in an elastic housing member. In operation, the dilator enlarges the canal in response to the laminate imbibing fluid and expanding, thereby exerting pressure on the elastic housing, which housing expands and urges the cervical canal to enlarge over time.

BRIEF DESCRIPTION OF THE DRAWINGS

In the drawings, which are not drawn to scale, but are set forth to illustrate various embodiments of the invention, the figures are as follows.

In the drawings and specification, like parts in related Figures are identified by like numbers, the terms appearing earlier in the specification and in the description of the Figures, as well as embodiments thereof, are further described elsewhere in the disclosure.

DETAILED DESCRIPTION OF THE INVENTION

Figure 1:
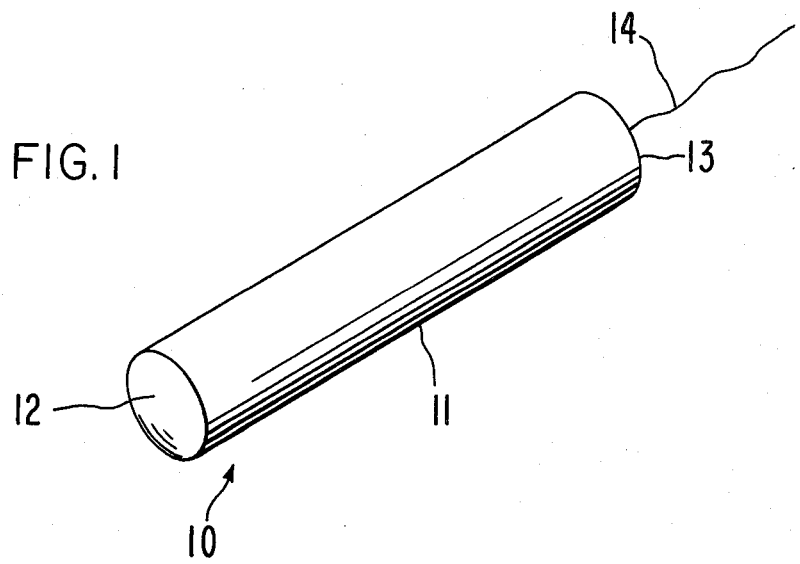
FIG. 1 is a front view of a cervical dilator made according to the invention.

Turning now to the drawings in detail, which are examples of new and useful dilators for enlarging the dimensions of the cervical canal, and which examples are not to be construed as limiting, one dilator is indicated in FIG. 1 by the numeral 10. In FIG. 1, dilator 10 consists essentially of a housing 11, sized, shaped and adapted for insertion into a cervical canal. Dilator 10 can embrace any shape such as round, oval, cylindrical or the like, and in a presently preferred embodiment the shape of dilator 10 will correspond to the naturally occurring shape of the cervical canal. Dilator 10 has a lead end 12 designed with a rounded configuration for substantially preventing injury that can occur during insertion, and a trailing end 13 equipped with a string 14 for manually removing dilator 10 from the canal.

Figure 2:
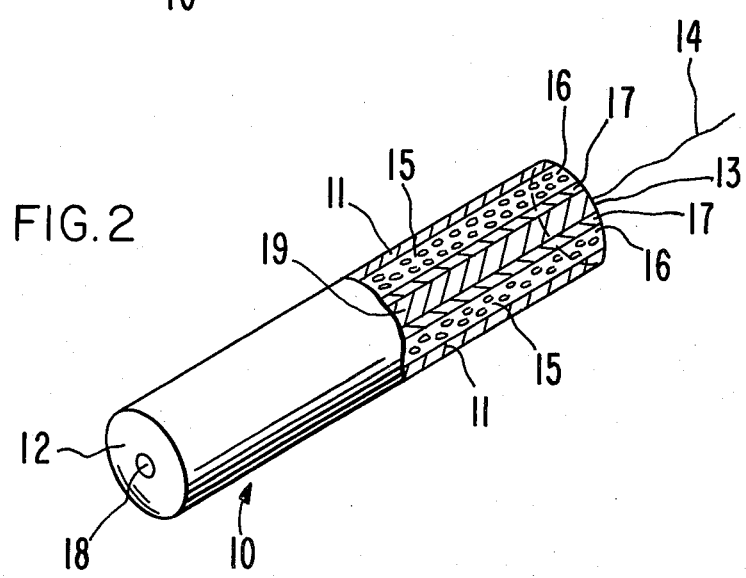
FIG. 2 is an opened view of the dilator of FIG. 1 through a—a thereof illustrating one structure of the dilator.

Referring to FIG. 2, dilator 10 of FIG. 1 is seen in opened-section along line 2—2 of FIG. 1. As seen in FIG. 2, dilator 10 comprises a housing 11 or body member formed of an elastomeric or other low-modulus material surrounding a laminate 15 comprising lamina 16 and lamina 17. Lamina 16 is positioned adjacent to the interior surface of housing 11 and it is formed of a swellable hydrophilic polymeric material. Lamina 17 is positioned distant from housing 11, and lamina 17 has a surface in laminar arrangement with lamina 16. Lamina 17 is formed of an absorbent porous or fibrous material capable of imbibing external fluid into housing 11. Fluid enters dilator 10 through opening 18 in lead-end 12, through an opening in trailing-end 13, not shown, or in an optional embodiment fluid enters dilator 10 through one or more holes in housing 11. Laminate 15 surrounds and is carried by support member 19. Member 19 is formed of a shape-retaining material that gives dimensions to dilator 10 and also provides physical support for housing 11 and laminate 15.

Figure 3:
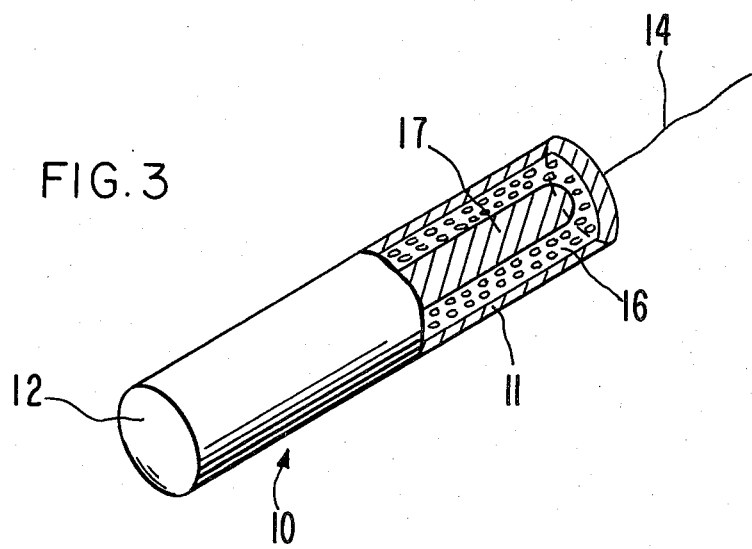
FIG. 3 is an opened view of the dilator of FIG. 1 through a—a thereof illustrating another structure of the dilator.

Dilator 10, as seen in FIG. 3, illustrates another embodiment provided according to the mode and manner of the invention. Dilator 10 of FIG. 3 is similar to dilator 10 of FIG. 2 as is possesses all the properties and advantages of the above-described dilator, even though it is manufactured without base member 19. Dilator 10, in this embodiment, is made with housing 11 and laminate 15. Laminate 15 comprises lamina 16 and lamina 17 rolled tightly into a rod-like structure and placed within housing 11. This embodiment inherently functions like a dilator made with member 19.

Figure 4:
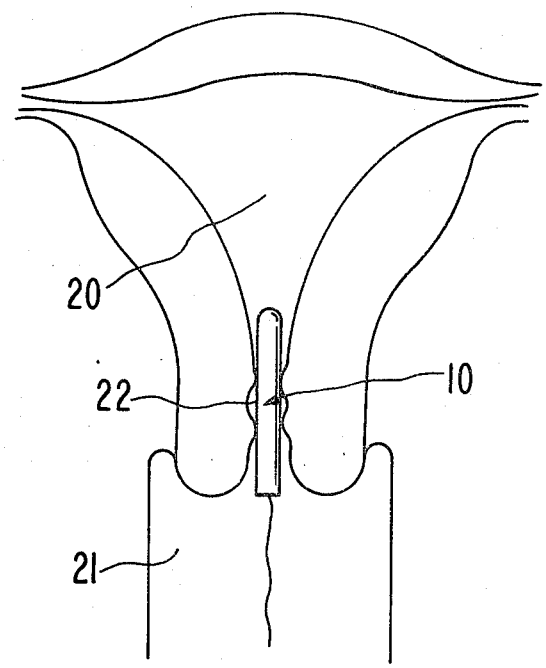
FIG. 4 is an illustration of the dilator of FIG. 1 depicting the dilator inserted into a cervical canal.
Figure 5:
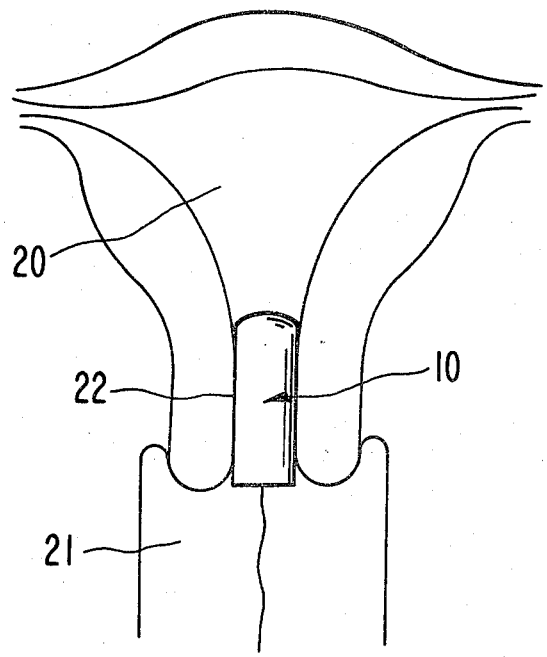
FIG. 5 is an illustration of the dilator of FIG. 4 showing the dilator in an expanded state thereby dilating the canal.

In FIGS. 4 and 5, dilator 10 is seen placed in cervical canal 22. Dilator 10 is inserted into canal 22 through vagina 21 until dilator 10 begins to enter uterus 20. In operation, dilator 10 functions by laminate 15 comprised of lamina 16 and lamina 17 slowly imbibing biological fluid into laminate 15, causing laminate 15 to swell and expand, mainly outwardly against housing 11, thereby exerting pressure against housing 11. In a dilator made with support member 19, inward expansion is restricted by member 19. The pressure applied against the interior surface of housing 11 causes dilator 10 to expand from an initial size in FIG. 4 to an enlarged size in FIG. 5, correspondingly dilating canal 22 at a controlled rate over time.

While FIGS. 1 through 5 are illustrative of various dilators that can be made according to the invention, it is to be understood these dilators are not to be construed as limiting, as they can take a wide variety of shapes, sizes and forms. Dilator 10 can be made for use in hospitals, nursing homes and clinics. In one presently preferred use dilator 10 is used for dilating a canal having limited passageway for subsequent insertion of an intrauterine contraceptive device into the uterus of a fertile woman.

ADDITIONAL DETAILS OF THE INVENTION

Dilator 10, as used for the purpose of this invention consists of housing 11 defining an internal space, with housing 11 manufactured from an elastomeric material that can expand in response to pressure applied against it, thereby increasing in size and correspondingly dilating the cervical canal. Typical elastomeric materials useful for this purpose include polymers such as natural rubber often identified by the synonyms poly(2-methyl-1,3-butadiene) and cis-1,4-poly-isoprene, gutta percha or trans-polyisoprene, cyclized rubber, synthetic isoprene rubber, butadiene rubber, styrene-butadiene rubber, nitrile rubber, chloroprene rubber, ethylene-propylene rubbers, butyl rubbers and the like. These materials are disclosed in *Handbook of Common Polymers*, by Scott and Roff, Sections 29 through 40, 1971, published by the Chemical Rubber Co., Cleveland, Ohio. In an optional embodiment, housing 11 can be manufactured with one or more passageways 18 that are formed when dilator 10 is in operation in the environment of use. In this latter embodiment, one potential passageway 18 is formed in housing 11 by eroding a water-soluble plug made of an erodible material. Typical materials include polyvinyl alcohol, gelatin, or the like, that can erode in a mammalian environment to form a small-diameter passageway.

Representative of absorbent materials suitable for forming lamina 17 are porous materials derived from animal and plant origins including wool, cotton, straw, flax and other vegetable fibers. Exemplary materials include cotton mats or pads of fibers, artificial regenerated cellulose sponge, blotting paper, tea bag paper and matted, felted, porous or fibrous sheets, or other means such as absorbent bleached and unbleached paper.

Representative of swellable hydrophilic materials suitable for forming lamina 16 are for example, lightly cross-linked, predominantly linear polymers, having cross-links formed by covalent or ionic bonds, and which polymers interact with biological fluids by swelling or expanding to some equilibrium state. These polymers swell to a very high degree without dissolution, usually exhibiting a 5 to 50 fold volume increase. Polymeric materials useful for this purpose include poly(hydroxyalkyl methacrylates), poly(N-vinyl-2-pyrrolidone), anionic and cationic hydrogels, polyelectrolyte complexes, poly(vinyl alcohol) having a low acetate residual and cross-linked with glyoxal, formaldehyde or glutaraldehyde, irradiation cross-linked poly(oxyethylene), methylcellulose cross-linked with a dialdehyde, a mixture of agar and sodium carboxymethyl cellulose, a water-insoluble, water swellable copolymer produced by forming a dispersion of finely divided copolymer of maleic anhydride with stryrene, ethylene, propylene, butylene or isobutylene cross-linked with from about 0.001 to about 0.5 mole of a polyunsaturated cross-linking agent per mole of maleic anhydride in the copolymer as disclosed in U.S. Pat. No. 3,989,589, water swellable polymers of N-vinyl lactams as disclosed in U.S. Pat. No. 3,992,562, and the like.

Representative of materials suitable for manufacturing support member 19 are materials that can be shaped and sized into a rod or a like shape, can carry laminate 15, and permit pressure to be exerted against it without any major changes in its shape or dimensions, thereby assuring that pressure generated in dilator 10 is exerted against expandable wall 11. Representative polymers suitable for forming housing 11 include polyethylene, polypropylene, polytetrafluoroethylene, polyamides, polyformaldehyde, polystyrene, polycarbonate, polyacrylate, polymethacrylate, polyacrylonitrile, poly(vinyl chloride), and the like.

The dilator of the invention is fabricated by standard techniques. For example, (1) a support member made of polyethylene is surrounded with (2) a monolithic laminate comprising teabag paper, having coated upon one of surface without filling the pores of the paper, a lamina of poly(vinyl alcohol) cross-linked with glyoxal, which laminate/support manufacture is surrounded, except for at least one opening for fluid imbibition, with (3) a thin film of natural rubber. Other procedures, as described in *Modern Plastics Encyclopedia*, Volume 46, 1969, which procedures are well-known to those skilled in the art, can be used to fabricate the dilator of the invention.

Although the foregoing invention has been described in detail, by way of embodiments, Figures and examples, it will be understood that certain changes and modifications may be practiced without departing from the scope and spirit of the invention.

We claim:
1. A cervical dilator sized, shaped and adapted to occlude the length of the cervical canal, comprising:
    (a) a base that permits pressure to be exerted against it without any major changes in its shape and dimensions and is made of a shape and dimension retaining material for imparting structural support to the dilator;
    (b) a laminate surrounding the base, said laminate adapted to absorb fluid and swell, and formed of a first lamina consisting of an absorbent material selected from the group consisting of porous and fibrous materials in contact with the base, which material is capable of imbibing an external fluid into the dilator and is in laminar arrangement with a second lamina formed of a different material consisting of a swellable hydrophilic material positioned distant from the base;

(c) a wall surrounding the laminate, said wall formed of a low modulus elastomeric material that expands in response to pressure applied by the laminate; and wherein, (d) when, the dilator is positioned in a cervical canal, the laminate imbibes fluid and swells with inward expansion restricted by the base, and concurrently applies outwardly an expanding pressure on the elastomeric wall, which wall then expands and exerts pressure against the cervical membrane, thereby dilating the canal over a period of time.

2. The cervical dilator according to claim 1 wherein the dilator is tubular-shaped and adapted to engage the biological membrane of a cervical canal.

3. The cervical dilator according to claim 1, wherein in operation when the dilator is in responsive relation in a cervical canal, the canal dilates concomitantly with the expansion of the dilator over a period of time.

4. The cervical dilator according to claim 1, wherein the absorbent material is a member selected from the group consisting of wool, cotton, felt, straw, flax, paper and mixtures thereof, and wherein the swellable, hydrophilic material is a cross-linked polymer selected from the group consisting of poly(hydroxyalkyl methacrylate), poly(N-vinyl-2-pyrrolidone), poly(electrolyte), poly(vinyl alcohol), and cellulose.

5. The cervical dilator according to claim 1, wherein the base is formed of a member selected from the group consisting of poly(ethylene), poly(tetrafluoroethylene), poly(amide), poly(formaldehyde), poly(styrene), poly(carbonate), poly(acrylate), poly(methacrylate), poly(acrylonitrile), and poly (vinyl alcohol).

6. The cervical dilator according to claim 1, wherein the elastomeric material is a member selected from the group consisting of natural rubber, gutta percha, cyclized rubber, isoprene rubber, butadiene rubber, styrene-butadiene rubber, nitrile rubber, chloroprene rubber, ethylene-propylene rubber, and butyl rubber.

7. The cervical dilator according to claim 1, wherein the dilator has at least one opening therein through which external fluid enters the dilator.

* * * * *